(12) United States Patent
Turturro et al.

(10) Patent No.: US 9,322,819 B2
(45) Date of Patent: Apr. 26, 2016

(54) METHOD AND APPARATUS PERTAINING TO TESTING MATERIAL QUALITY

(71) Applicant: Medline Industries, Inc., Mundelein, IL (US)

(72) Inventors: Michael Turturro, Chicago, IL (US); Andrew Nachenberg, Grayslake, IL (US)

(73) Assignee: Medline Industries, Inc., Mundelein, IL (US)

( * ) Notice: Subject to any disclaimer, the term of this patent is extended or adjusted under 35 U.S.C. 154(b) by 209 days.

(21) Appl. No.: 14/225,979

(22) Filed: Mar. 26, 2014

(65) Prior Publication Data
US 2015/0276569 A1    Oct. 1, 2015

(51) Int. Cl.
*G01N 3/08* (2006.01)
*G01N 33/34* (2006.01)
*G01N 3/42* (2006.01)

(52) U.S. Cl.
CPC .................. *G01N 33/34* (2013.01); *G01N 3/42* (2013.01); *G01N 3/08* (2013.01)

(58) Field of Classification Search
CPC ............. G01N 3/08; G01N 3/36; G01N 3/42; G01B 5/30
USPC .................... 73/821, 818, 788, 790, 813, 760
See application file for complete search history.

(56) References Cited

U.S. PATENT DOCUMENTS

| | | | | |
|---|---|---|---|---|
| 6,050,149 A | * | 4/2000 | Yoshizawa | G01N 3/20 73/812 |
| 2009/0199663 A1 | * | 8/2009 | Kaneda | G01N 3/062 73/866 |

OTHER PUBLICATIONS

ASTM F1306 Slow Rate Penetration Resistance of Flexible Barrier Films and Laminate from internet page http://www.instron.us/wa/solutions/ASTM_F1306_SlowRatePenetrationResistance_FlexibleBarrierFilmsLaminates.aspx.
Omega Digital Force Gages DFG21 Series from internet page http://www.omega.com/pptst/DFG21.html.

* cited by examiner

*Primary Examiner* — Lisa Caputo
*Assistant Examiner* — Nigel Plumb
(74) *Attorney, Agent, or Firm* — Fitch, Even, Tabin & Flannery LLP

(57) ABSTRACT

A quality-control device comprises a housing, a biasing member disposed within the housing, and a reciprocating puncturing member that is configured and oriented to selectively move inwardly of the housing in opposition to the biasing member. A maximum-compression indicator is configured to move inwardly of the housing in tandem with the puncturing member and a gauge serves to correlate a particular location of the maximum-compression indicator to a corresponding measure of compression as corresponds to a material being tested for quality. By one approach the indicator moves in response to inward movement of the puncturing member but is also configured to not move when the puncturing member moves outwardly of the housing. So configured the maximum-compression indicator will remain located at a point that corresponds to the furthest inward incursion of the puncturing member in opposition to the biasing member when the user presses the puncturing member against the material.

14 Claims, 8 Drawing Sheets

METHOD AND APPARATUS PERTAINING TO TESTING MATERIAL QUALITY

TECHNICAL FIELD

This invention relates generally to testing the quality of a given material and more particularly to testing the material's strength.

BACKGROUND

It is known to select a given material as a function, at least in part, of a given corresponding use and purpose. For example, an enterprise may select a given grade and composition of corrugated board to use when packaging a particular product to ensure adequate protection for the product during an anticipated shipping and handling process.

At the same time, however, cost considerations often compel the enterprise to seek materials that, while adequate to the task, are not unduly over-engineered for the desired purpose. Using a material that is unduly strong for a given purpose, for example, will typically result in an uncompetitively-high cost for the product in question.

Accordingly, many enterprises specify particular materials for particular purposes to ensure both adequate performance and appropriate cost.

This balancing of considerations, however, can increase the importance of quality control. In particular, for example, it can be important that the packaging material perform within its stated specifications. When quality control slips the packaging material may fail to perform as expected and thereby expose the corresponding product to increased risk of damage.

There are known ways by which packaging materials and the like can be tested to assess, for example, their relative strength. Unfortunately, these approaches are typically not well suited for use in the field (such as, for example, at a packing facility that employs the packaging material when packing corresponding products). As a result, ensuring the quality of packaging material can prove challenging and hence is often left unknown and uncertain.

BRIEF DESCRIPTION OF THE DRAWINGS

The above needs are at least partially met through provision of the method and apparatus pertaining to testing material quality described in the following detailed description, particularly when studied in conjunction with the drawings, wherein.

Figures 1, 2:
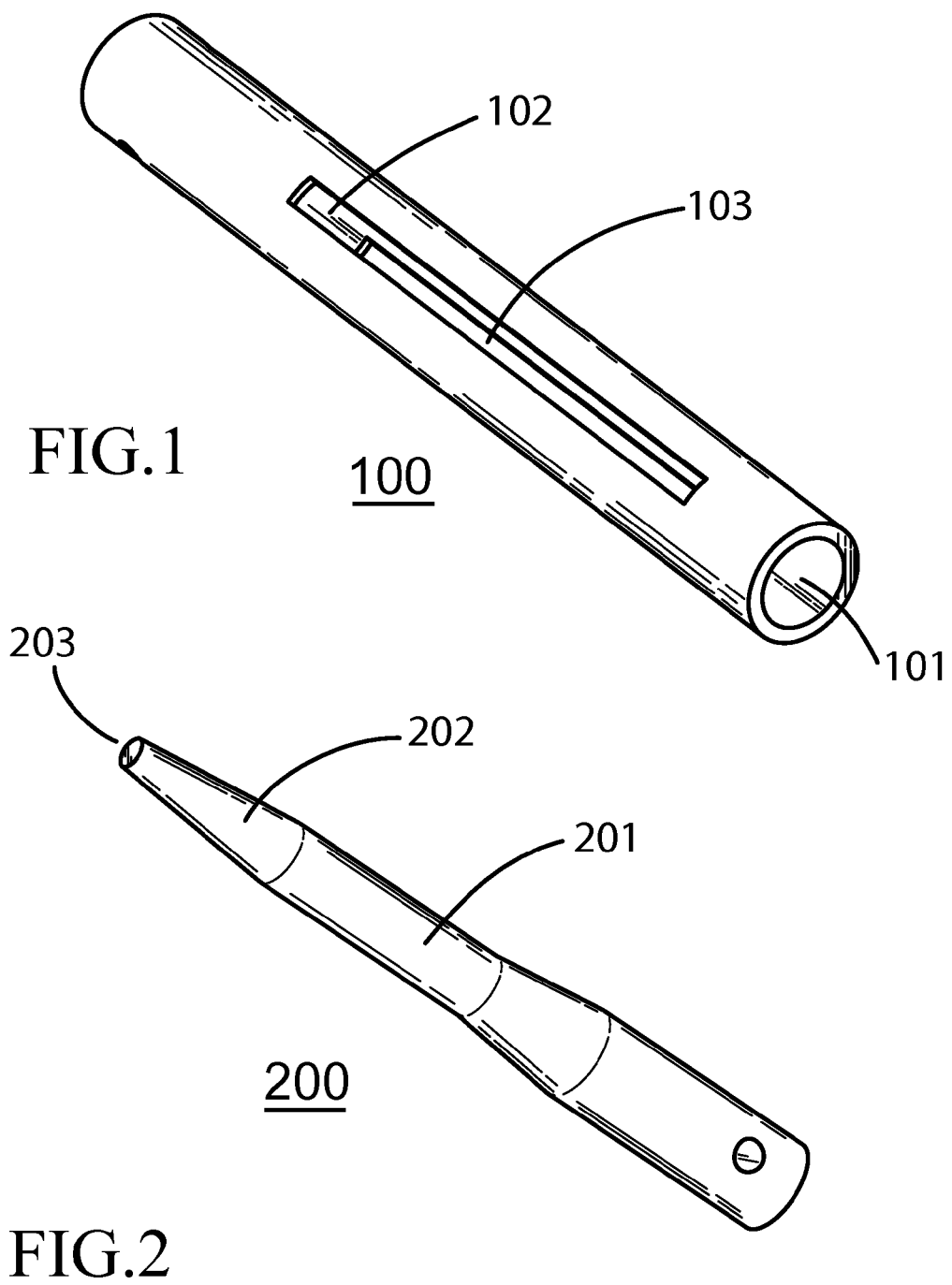
FIG. 1 comprises a perspective view as configured in accordance with various embodiments of the invention.
FIG. 2 comprises a perspective view as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a quality-control device comprises a housing, a biasing member disposed within the housing, and a reciprocating puncturing member that is configured and oriented to selectively move inwardly of the housing in opposition to the biasing member. A maximum-compression indicator is configured to move inwardly of the housing in tandem with the reciprocating puncturing member and a gauge serves to correlate a particular location of the maximum-compression indicator to a corresponding measure of compression as corresponds to a corrugated board being tested for material quality.

By one approach the aforementioned maximum-compression indicator moves in response to inward movement of the reciprocating puncturing member but is also configured to not move when the reciprocating puncturing member moves outwardly of the housing. So configured the maximum-compression indicator will typically remain located at a point that corresponds to the furthest inward incursion of the reciprocating puncturing member in opposition to the biasing member as the user presses the reciprocating puncturing member against the corrugated board.

In particular, when the reciprocating puncturing member eventually punctures the corrugated board (hence releasing force on the reciprocating puncturing member and allowing the latter to return to a pre-compression state) the maximum-compression indicator will remain even as the reciprocating puncturing member is urged outwardly by the biasing member to thereby indicate the furthest point reached by the reciprocating puncturing member while being pressed against the corrugated board.

By one approach the housing can further comprise a gauge to thereby provide a useful metric by which to judge and evaluate that furthest point reached by the reciprocating puncturing member as described above. Such a gauge can be relatively simple and/or conclusory (such as a gauge that simply indicates whether a given point represents an acceptable level of material quality or not) or more specific and quantitative (such as a gauge that provides a scale marked with force metrics to thereby associate the aforementioned furthest point with a particular standard (or non-standard, if desired) metric.

Such a device can be readily formed of relatively inexpensive materials. Such a device can also be used by someone with very little in the way of training or background knowledge regarding the science and industry of packaging materials. It will also be appreciated that such a device can yield useful results in a matter of seconds and in essentially any application setting.

Accordingly, these teachings facilitate an easy, inexpensive, and nearly universal way to test the quality of materials such as (but not limited to) corrugated board in essentially any location or setting and by virtually anyone. Such a capability, in turn, greatly increases the ability of the user to ensure that the materials being employed in fact meet their agreed-to or otherwise represented quality standards.

These and other benefits may become clearer upon making a thorough review and study of the following detailed description. Referring now to the drawings, and in particular to FIG. 1, a housing 100 can comprise a generally cylindrically-shape member having an open first end 101 and a cavity 102 formed axially therein. In this particular example the end opposite the open first end 101 is closed. In this illustrative example the housing 100 also includes a pair of slots 103 formed through the housing wall on opposing sides of the housing 100. The housing 100 can be formed of any material of choice include a variety of metals and plastics.

The length of the housing 100 (as well as its width) can vary as desired. Similarly, the dimensions of the slots 103 (and whether the two slots 103 are essentially identical to one another or vary with respect to length, width, and form) can vary as desired. In this illustrative example, the two slots 103 are of identical length and width and are disposed laterally opposite one another in registered alignment.

FIG. 2 presents a reciprocating puncturing member 200 sized and shaped to fit within the cavity 102 of the housing 100. In particular, the main body 201 of the reciprocating puncturing member 200 comprises a cylinder that slides substantially conformally into the open first end 101 of the housing 100 to thereby accommodate having the reciprocating puncturing member 200 slide back and forth in a reciprocating manner with respect to the housing 100.

In this illustrative example the reciprocating puncturing member 200 has a puncturing end 202 that is cone shaped and that includes a tip 203 that can be more spherically shaped. The width of this tip 203 and its radius of curvature can vary as desired to suit the needs of a particular application setting.

By one approach the aforementioned tip 203 comprises an integral part of the reciprocating puncturing member 200. By another approach, if desired, the tip 203 can be selectively separable from the main body 201 to thereby permit tips 203 having different dimensions and characteristics to be selectively used with the same device. A removable tip 203 can connect to the main body 201 using any of a variety of selective attachment mechanisms such as, but not limited to, snaps, threaded engagement members, clips, and so forth.

Similar to the housing 100 the reciprocating puncturing member 200 can be formed of one or more materials of choice. Examples in these regards include but are not limited to any of a variety of metals and plastics.

Figure 3:
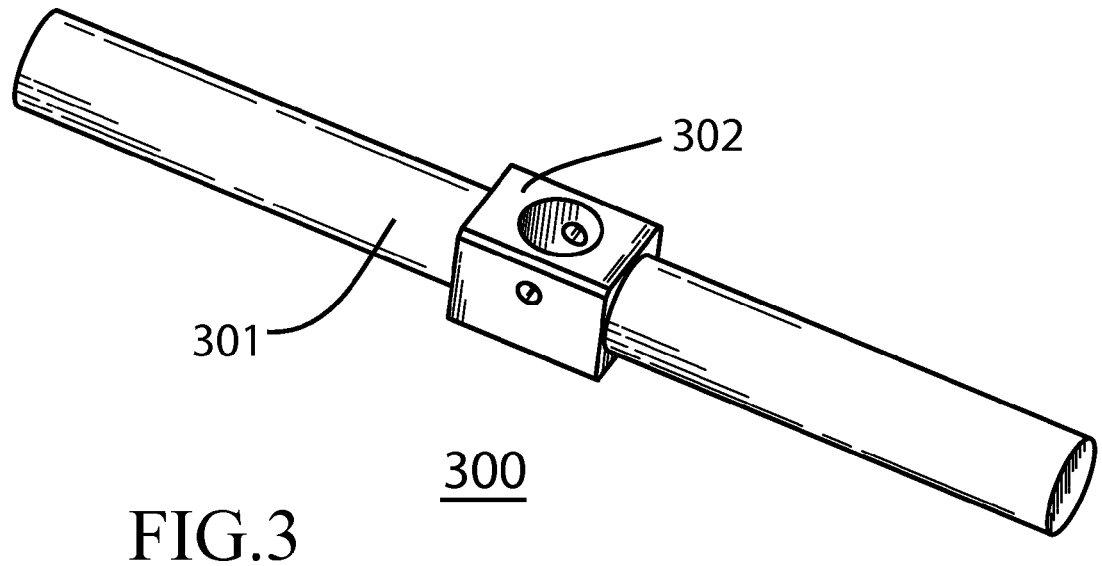
FIG. 3 comprises a perspective view as configured in accordance with various embodiments of the invention.
Figure 4:
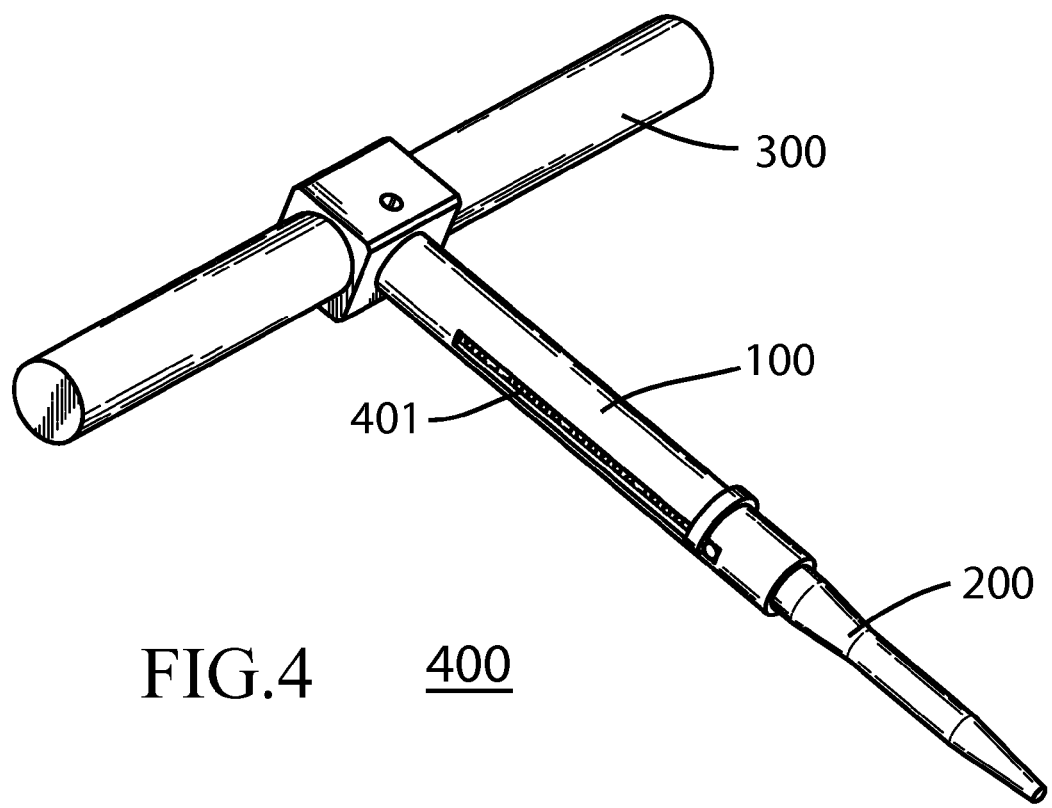
FIG. 4 comprises a perspective view as configured in accordance with various embodiments of the invention.

FIG. 3 presents a hand-graspable handle 300 comprising a cylinder 301 having an opening 302 formed laterally within the cylinder 301 midway along the length thereof. So configured, and as shown in FIG. 4, the closed end of the housing 100 can be disposed within the aforementioned opening 302 to thereby affix the hand-graspable handle 300 to the housing 100.

By one approach the hold 302 and the housing 100 can be sized and shaped to provide for a firm friction fit when so disposed to thereby hold these two components together. These teachings will readily accommodate other approaches in these regards, however. For example, threaded surfaces can serve to permit these two components to be screwed together. By another approach an adhesive of choice can serve to adhere the housing 100 to the hand-graspable handle 300.

So configured, the resultant quality-control device 400 can be readily gripped by the hand-graspable handle 300 and wielded as described herein to urge the reciprocating puncturing member 200 against a material to be tested. With this purpose in mind it will be understood that these teachings will readily accommodate a wide variety of handle form factors.

A biasing member 401 serves to oppose inward movement of the reciprocating puncturing member 200 with respect to the housing 100. In this illustrative example this biasing member 401 comprises a spring that fits within the cavity 102 of the housing 100. For many application settings it will serve well for the spring to comprise a calibrated spring; i.e., a spring that compresses in a reliable and known way in response to corresponding amounts of force. For example, a calibrated spring may collapse one inch for each 12.6 pounds of applied force. By one approach the spring comprises a calibrated compression spring having a rated tolerance of no more than about plus/minus ten percent.

So configured, the reciprocating puncturing member 200 will slide into the housing 100 as a user applies force to the hand-graspable handle 300 while pushing the reciprocating puncturing member 200 against a given surface. If and when the reciprocating puncturing member 200 punctures that surface the biasing member 401 (which can be co-axially aligned with the reciprocating puncturing member 200 as illustrated) will urge the reciprocating puncturing member 200 to its initial state as the spring returns to its uncompressed state.

Figure 5:
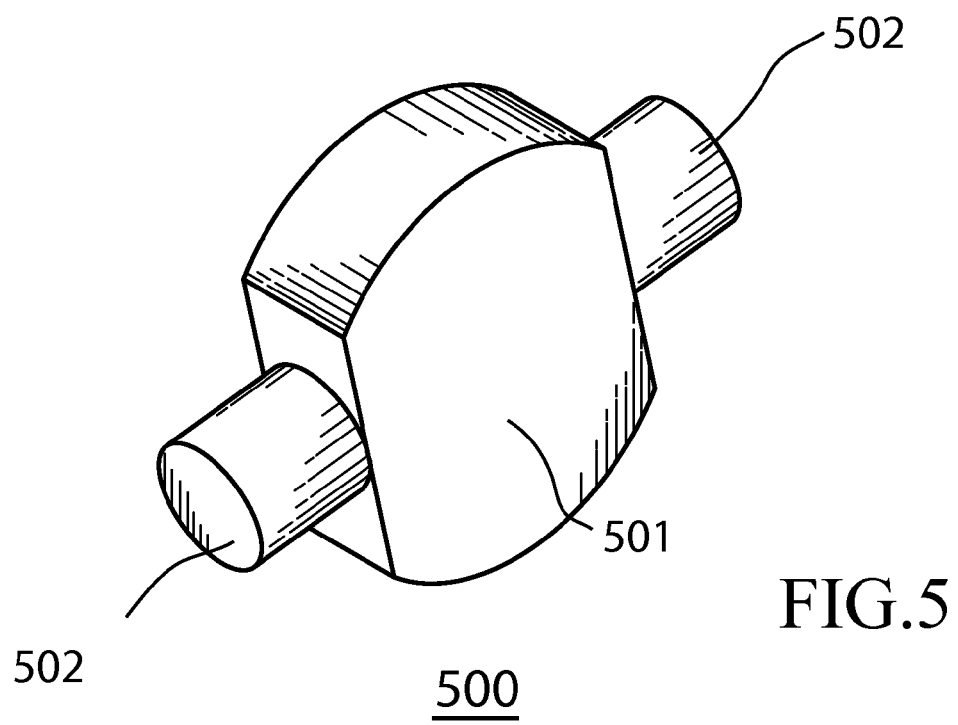
FIG. 5 comprises a perspective view as configured in accordance with various embodiments of the invention.

FIG. 5 presents a spring plate 500 that can serve in conjunction with the aforementioned quality-control device 400. This spring plate 500 includes a somewhat disc-shaped portion 501 that fits conformally within the cavity 102 of the housing 100, though not so tightly as to impede movement of the reciprocating puncturing member 200 back and forth within the housing 100. In addition, in this example the spring plate 500 also includes tabs 502 that extend outwardly on opposing sides of the disc-shaped portion 501. So configured, and as will be illustrated further below, these tabs 502 can extend through the slots 103 of the housing 100. By one approach, these tabs 502 are sized to fit conformally through those slots 103 though again not so tightly as to impede free reciprocating movement of the puncturing member 200.

This spring plate 500 can again be comprised of any useful material including any of a variety of metals and/or plastics.

Such a spring plate 500 can be disposed within the housing 100 between the reciprocating puncturing member 200 and the biasing member 401 as disclosed below in more detail. So disposed, the spring plate 500 will move back and forth within the housing 100 as the reciprocating puncturing member 200 moves into and out of the housing as described herein. More particularly, the spring plate 500, including the aforementioned tabs 502, will track the movement of the reciprocating puncturing member 200 during use of the device 400.

Figure 6:
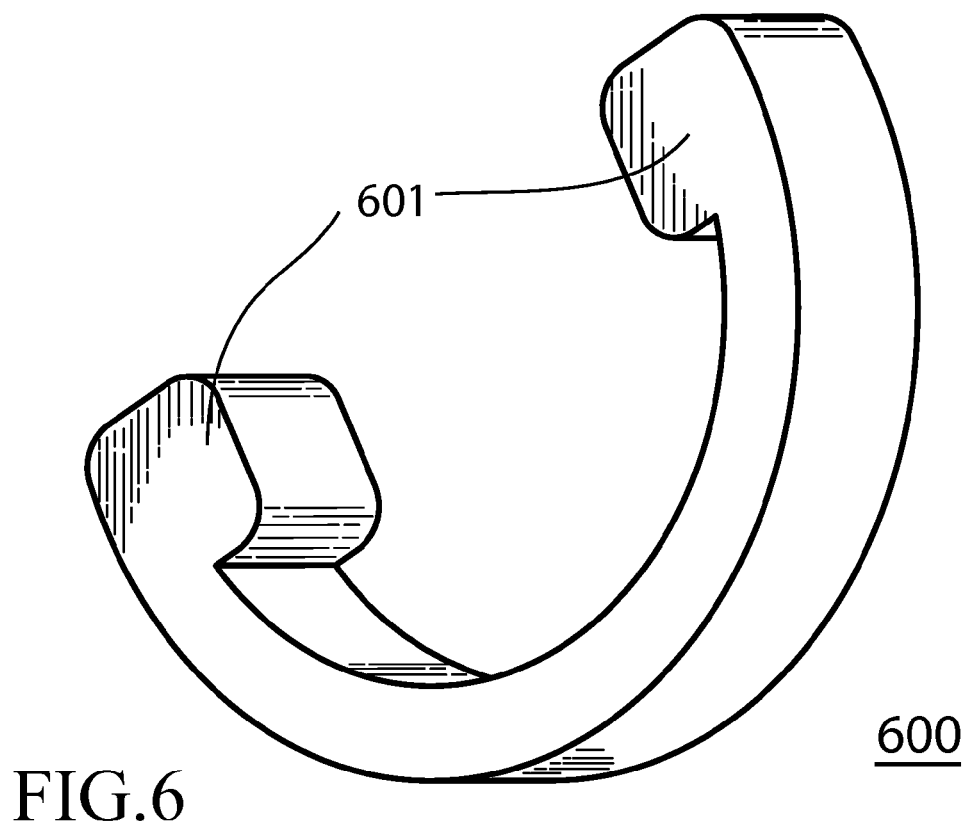
FIG. 6 comprises a perspective view as configured in accordance with various embodiments of the invention.

These teachings also provide for employing one or more maximum-compression indicators that are configured to move inwardly/upwardly of the housing 100 as the reciprocating puncturing member 200 moves inwardly but that do not move when the reciprocating puncturing member 200 moves outwardly of the housing 100 as the biasing member 401 forces the former from within the housing 100. FIG. 6 provides one illustrative example in these regards.

In this example, the maximum-compression indicator 600 comprises a half ring having an inwardly-directed flange 601 at the terminating ends thereof. The half ring is generally sized to fit around the exterior of the housing 100 and the flanges 601 are sized and configured to interact with the aforementioned tabs 502 of the spring plate 500. As will be shown below, the spring plate 500 will urge the maximum-compression indicator 600 along the length of the housing 100 when the reciprocating puncturing member 200 is urged within the housing 100. As the reciprocating puncturing member 200 and spring plate 500 return to their quiescent positions of rest, however, the maximum-compression indicator 600 will remain at its final point of movement, which final point corresponds to when the device 400 experienced its maximum compression.

Notwithstanding the specific technical details of the example just provided, it will be understood that these teachings will accommodate a variety of approaches in these regards. These teachings do not require, for example, that the indicator have a half-ring form factor. By one approach, for example, the indicator could comprise a slide indicator that sits in one of the slots (103) of the housing (100).

FIGS. 7-12 provide a specific example in these regards. It will be understood that no particular limitations are intended by way of the specificity of this example.

Figure 7:
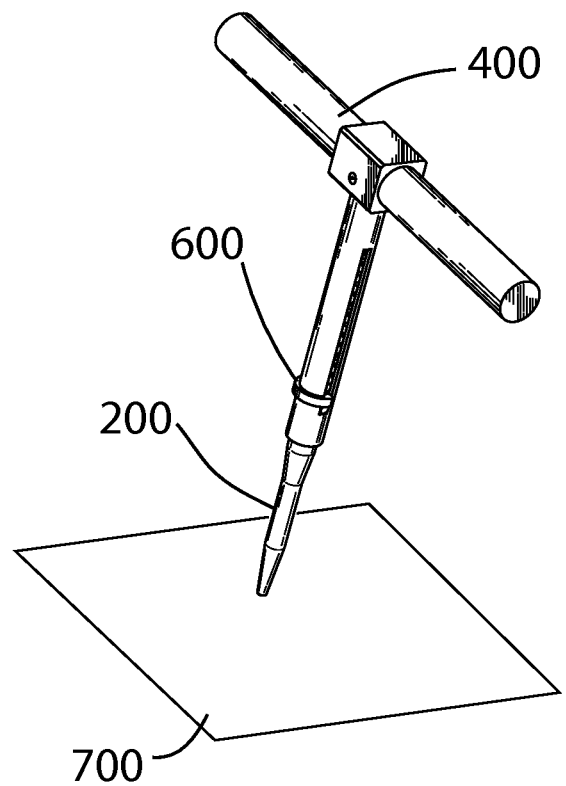
FIG. 7 comprises a perspective view as configured in accordance with various embodiments of the invention.
Figure 8:
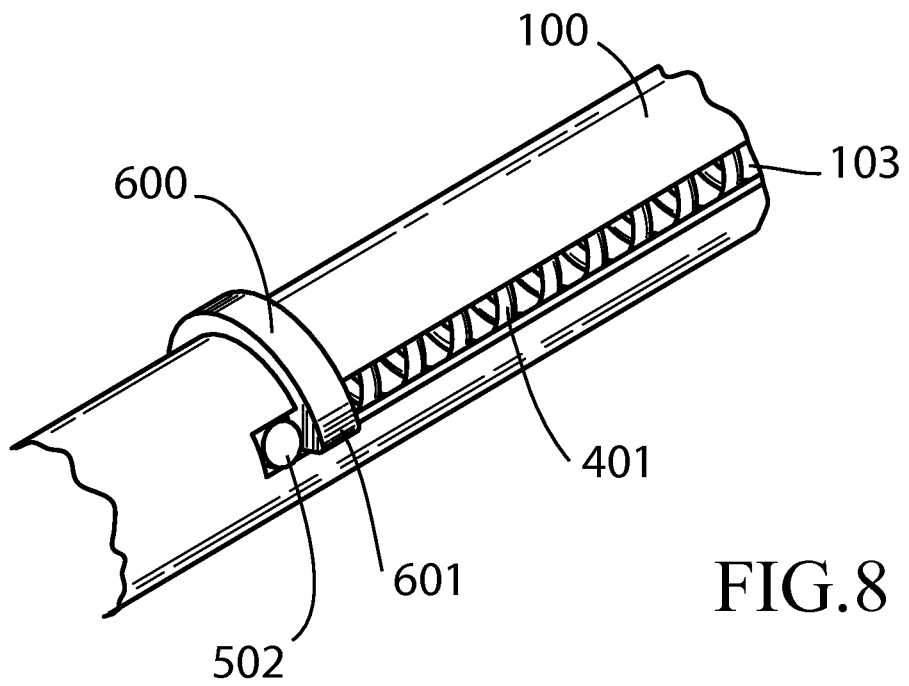
FIG. 8 comprises a detail perspective view as configured in accordance with various embodiments of the invention.

In FIG. 7 the device 400 is disposed perpendicularly (or at least nearly so, say within a few degrees) to a material 700 to be tested. This material 700 can comprise, for example, corrugated board. These teachings can be applied with a variety of other materials, however, including non-corrugated material as well as materials not comprised of paper-like content such as a variety of foils, films, and even taut fabrics. The device 400 is not yet being pressed against the material 700 and therefore the maximum-compression indicator 600 is not yet moved from its starting point as shown in more detail in FIG. 8.

Figure 9:
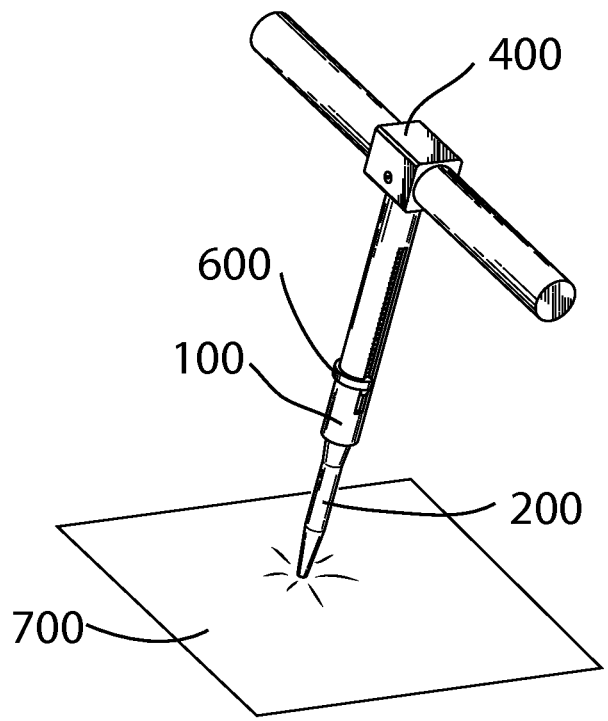
FIG. 9 comprises a perspective view as configured in accordance with various embodiments of the invention.
Figure 10:
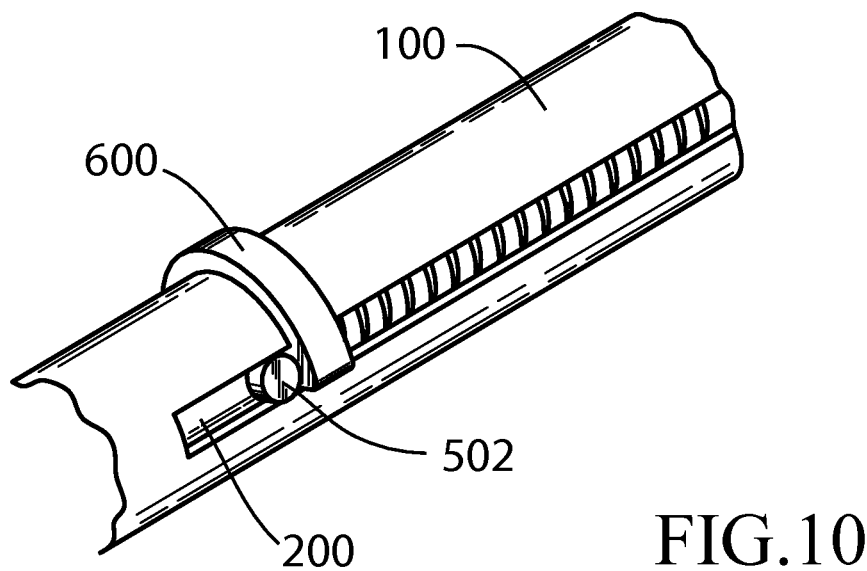
FIG. 10 comprises a detail perspective view as configured in accordance with various embodiments of the invention.

Referring now to FIGS. 9 and 10, as the device 400 is pressed against the material 700 the reciprocating puncturing member 200 enters the housing 100 and accordingly pushes the aforementioned spring plate 500 and maximum-compression indicator 600 along the length of the housing 100 as the biasing member 401 compresses.

Figure 11:
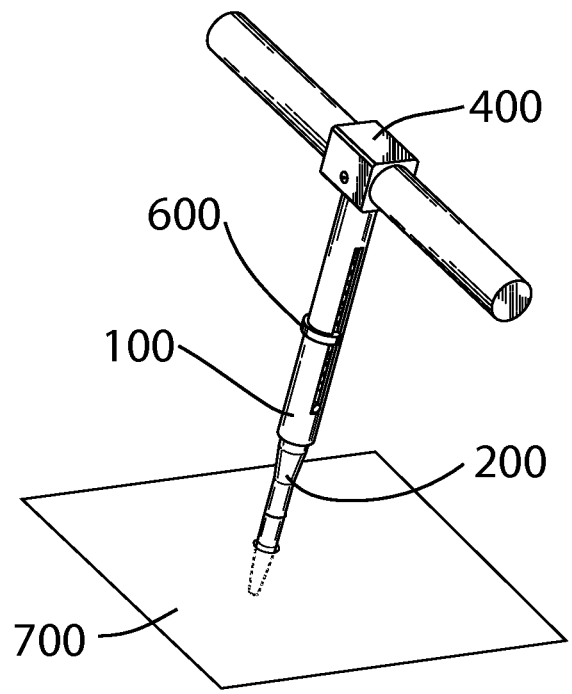
FIG. 11 comprises a perspective view as configured in accordance with various embodiments of the invention.
Figure 12:
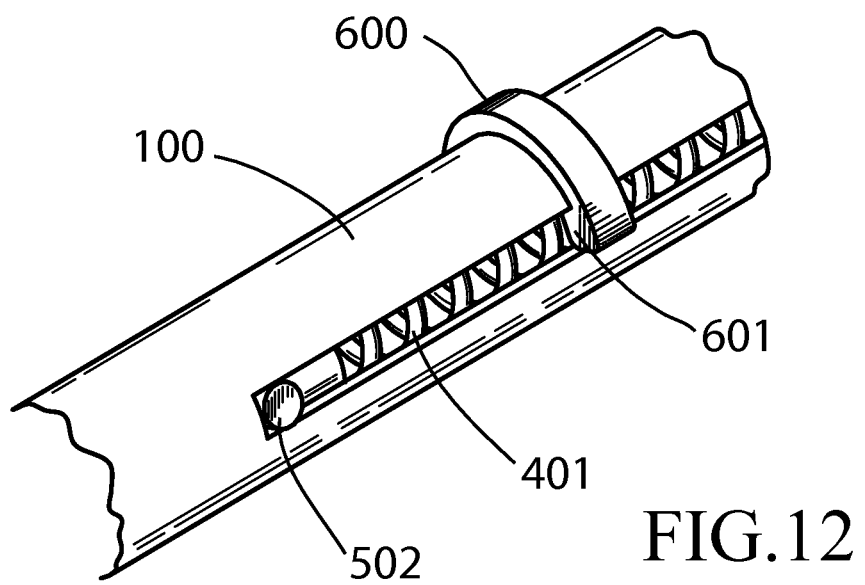
FIG. 12 comprises a detail perspective view as configured in accordance with various embodiments of the invention.

As shown in FIGS. 11 and 12, eventually the force being applied is sufficient to permit the reciprocating puncturing member 200 to puncture the material 700. When this happens the biasing member 401 urges the reciprocating puncturing member 200 and the spring plate 500 back to their fully-extended positions. The biasing member 401, however, does not act (directly or indirectly) upon the maximum-compression indicator 600 when uncompressing. Accordingly, as shown in FIG. 12, the maximum-compression indicator 600 remains where it was when the puncture occurred and the reciprocating puncturing member 200 began returning to its position of rest.

Figure 13:
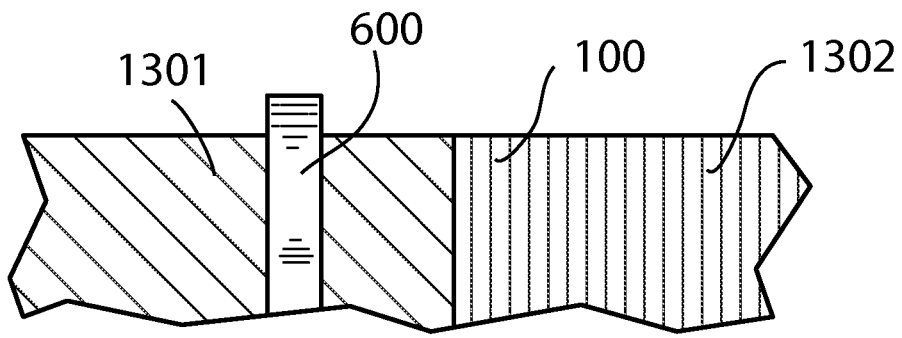
FIG. 13 comprises a detail top plan view as configured in accordance with various embodiments of the invention.

By one approach a gauge can serve to correlate particular locations of the maximum-compression indicator 600 (with respect to the housing 100) to a corresponding measure of compression as corresponds to the material 700 being tested. FIG. 13 provides one simple example in these regards. In this example the housing 100 has a first portion 1301 colored green and another portion 1302 colored red. When the maximum compression recorded by the maximum-compression indicator 600 lies in common with the green area 1301, the tested material 700 has performed satisfactorily. When, however, the maximum compression recorded by the maximum-compression indicator 600 lies in common with the red area 1302, the test material 700 fails the quality test. Such a pass/fail approach can serve well in an application setting where only a single material having a single corresponding compression rating is to be tested.

Figure 14:
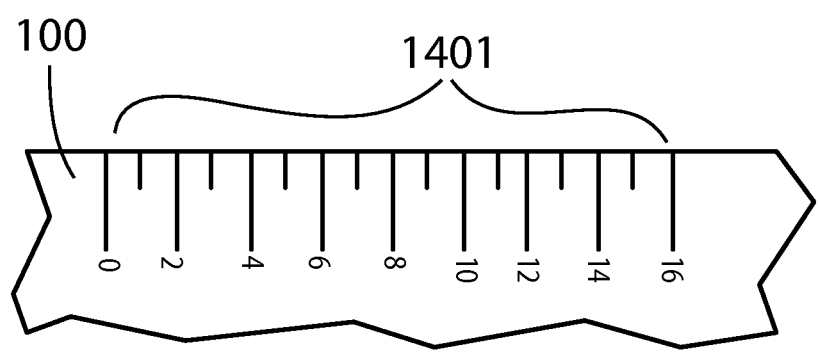
FIG. 14 comprises a detail top plan view as configured in accordance with various embodiments of the invention.

FIG. 14 provides another example in these regards. In this example, the housing 100 has a calibrated scale 1401 disposed thereon. This scale 1401 provides corresponding values that can be associated with the position of the maximum-compression indicator 600 to thereby provide a specific standard (or non-standard, if desired) measure of the compression strength of the material 700 being tested.

Such a device 400 can be economically manufactured and easily and reliably carried and utilized by even relatively untrained persons to test, in the field and where and when desired, the quality of a variety of materials including a variety of packaging materials such as corrugated board. These capabilities, in turn, can help to ensure that only materials of appropriate quality are employed when packing and/or packaging various products to thereby help ensure the safe shipping, handling, and storage of those products.

Figure 15:
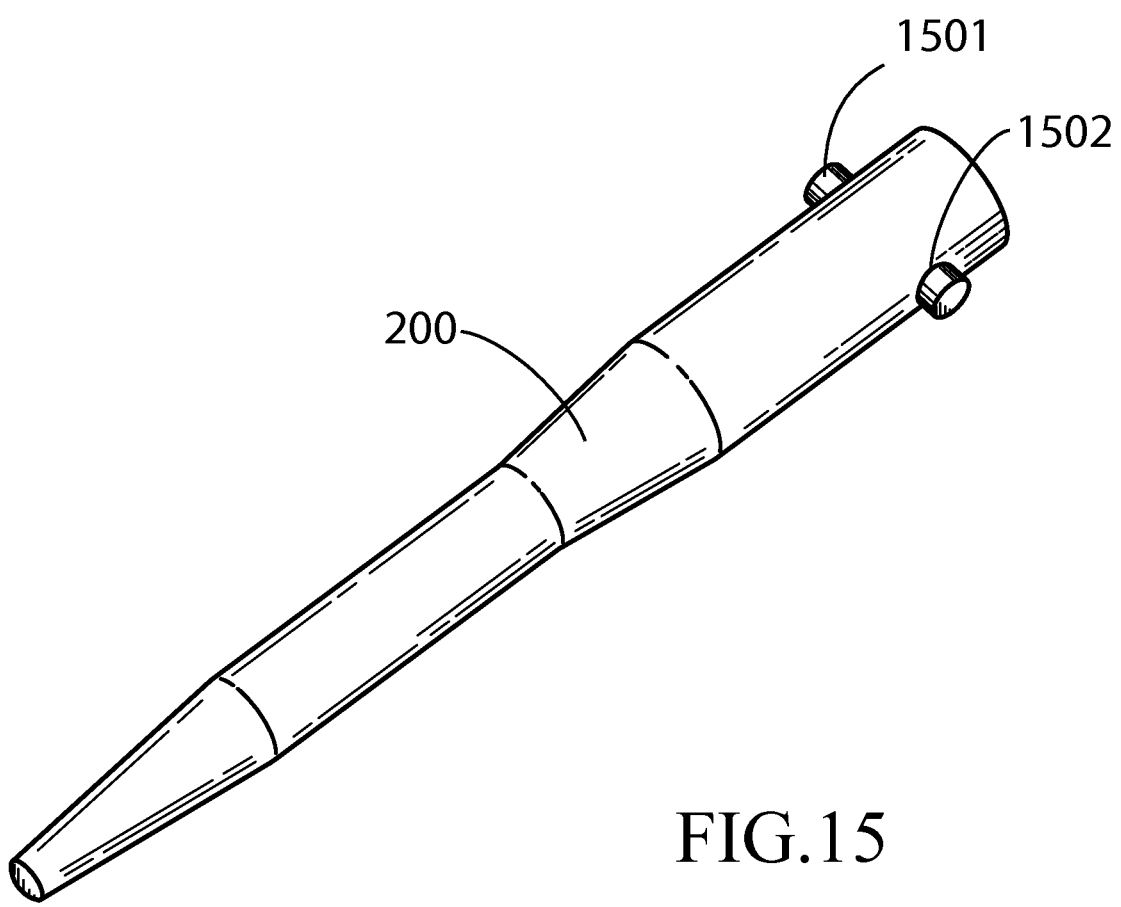
FIG. 15 comprises a detail perspective view as configured in accordance with various embodiments of the invention.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept. As but one example in these regards, and referring now to FIG. 15, instead of employing a physically discrete spring plate 500 as described above, the non-puncturing end of the reciprocating puncturing member 200 can effectively serve in these regards. In this example, the above-described tabs 502 of the spring plate 500 are effectively served by use of a pin 1501 that extends laterally through a hole 1502 in the reciprocating puncturing member 200.

What is claimed is:

1. A quality-control device to test material quality of corrugated board, the quality-control device comprising:
   a housing;
   a reciprocating puncturing member;
   a biasing member configured to oppose inward movement of the reciprocating puncturing member with respect to the housing;
   a maximum-compression indicator configured to move inwardly of the housing with the reciprocating puncturing member;
   a gauge configured to correlate a particular location of the maximum-compression indicator to a corresponding measure of compression as corresponds to the corrugated board.

2. The quality-control device of claim 1 wherein the biasing member is co-axially aligned with the reciprocating puncturing member.

3. The quality-control device of claim 1 wherein the maximum-compression indicator comprises a hand-resettable maximum-compression indicator.

4. The quality-control device of claim 3 wherein the maximum-compression indicator is further configured to not move when the reciprocating puncturing member moves outwardly of the housing.

5. The quality-control device of claim 1 wherein the biasing member comprises a spring.

6. The quality-control device of claim 5 wherein the spring comprises a calibrated compression spring having a rated tolerance of no more than plus/minus ten percent.

7. The quality-control device of claim 1 and further comprising:
a hand-graspable handle operably coupled to the housing to permit a user to apply the reciprocating puncturing member to the corrugated board to test the material quality of the corrugated board.

8. A method comprising:
providing a housing;
providing a reciprocating puncturing member;
disposing a biasing member to oppose inward movement of the reciprocating puncturing member with respect to the housing;
disposing a maximum-compression indicator to move inwardly of the housing with the reciprocating puncturing member;
disposing a gauge to correlate a particular location of the maximum-compression indicator to a corresponding measure of compression as corresponds to a sample of corrugated board.

9. The method of claim 8 wherein the biasing member is co-axially aligned with the reciprocating puncturing member.

10. The method of claim 8 wherein the maximum-compression indicator comprises a hand-resettable maximum-compression indicator.

11. The method of claim 8 wherein the maximum-compression indicator is further configured to not move when the reciprocating puncturing member moves outwardly of the housing.

12. The method of claim 8 wherein the biasing member comprises a spring.

13. The method of claim 12 wherein the spring comprises a calibrated compression spring having a rated tolerance of no more than ten percent.

14. The method of claim 8 and further comprising:
operably coupling a hand-graspable handle to the housing.

\* \* \* \* \*